United States Patent
Miyake et al.

(10) Patent No.: US 9,845,304 B2
(45) Date of Patent: Dec. 19, 2017

(54) METHOD FOR PRODUCING ASYMMETRIC CONJUGATED DIYNE COMPOUND AND METHOD FOR PRODUCING Z,Z-CONJUGATED DIENE COMPOUND USING THE SAME

(71) Applicant: Shin-Etsu Chemical Co., Ltd., Tokyo (JP)

(72) Inventors: Yuki Miyake, Joetsu (JP); Takeshi Kinsho, Joetsu (JP); Miyoshi Yamashita, Joetsu (JP); Naoki Ishibashi, Joetsu (JP); Yusuke Nagae, Joetsu (JP); Akihiro Baba, Joetsu (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 11 days.

(21) Appl. No.: 15/014,598

(22) Filed: Feb. 3, 2016

(65) Prior Publication Data

US 2016/0229829 A1 Aug. 11, 2016

(30) Foreign Application Priority Data

Feb. 6, 2015 (JP) .................................. 2015-022119

(51) Int. Cl.

| C07C 17/266 | (2006.01) |
|---|---|
| C07C 17/269 | (2006.01) |
| C07C 2/86 | (2006.01) |
| C07C 29/10 | (2006.01) |
| C07C 29/32 | (2006.01) |
| C07C 41/48 | (2006.01) |
| C07C 45/26 | (2006.01) |
| C07C 45/51 | (2006.01) |
| C07C 67/08 | (2006.01) |
| C07C 67/40 | (2006.01) |
| C07D 309/12 | (2006.01) |

(52) U.S. Cl.

CPC ............ *C07D 309/12* (2013.01); *C07C 2/861* (2013.01); *C07C 17/266* (2013.01); *C07C 17/269* (2013.01); *C07C 29/103* (2013.01); *C07C 29/32* (2013.01); *C07C 41/48* (2013.01); *C07C 45/26* (2013.01); *C07C 45/515* (2013.01); *C07C 67/08* (2013.01); *C07C 67/40* (2013.01); *C07B 2200/09* (2013.01); *C07C 2527/122* (2013.01)

(58) Field of Classification Search

CPC ..... C07C 17/266; C07C 17/269; C07C 2/861; C07C 29/103; C07C 29/32; C07C 41/48; C07C 45/26; C07C 45/515; C07C 67/08; C07C 67/40; C07D 309/12

See application file for complete search history.

(56) References Cited

FOREIGN PATENT DOCUMENTS

WO WO 2008/154642 A2 12/2008

OTHER PUBLICATIONS

Lennox et al., "Selection of boron reagents for Suzuki-Miyaura coupling," Chem. Soc. Rev., 2014, 43, 412-443.*
Marino et al., "Bulky Trialkylsilyl Acetylenes in the Cadiot-Chodkiewicz Cross-Coupling Reaction," J. Org. Chem., 2002, 67 (19), pp. 6841-6844.*
European Search Report Corresponding to European Patent Application No. 16 15 3798; Dated: Jun. 2, 2016; 5 Pages.
Chen et al. "Transition-Metal-Free Homocoupling of 1-Haloalkynes: A Facile Synthesis of Symmetrical 1,3-Diynes", J. Org. Chem., 2010, 75(19), pp. 6700-6703.
Marino et al. "Bulky Trialkylsilyl Acetylenes in the Cadiot-Chodkiewicz Cross-Coupling Reaction", J. Org. Chem., 2002, 67(19), pp. 6841-6844.
Shi et al. "Investigation of an Efficient Palladium-Catalyzed C(sp)-C(sp) Cross-Coupling Reaction Using Phosphine-Olefin Ligand: Application and Mechanistic Aspects", J. Am. Chem. Soc., 2008, 130(44), pp. 14713-14720.

* cited by examiner

*Primary Examiner* — Pancham Bakshi
*Assistant Examiner* — Mark Luderer
(74) *Attorney, Agent, or Firm* — Myers Bigel, P.A.

(57) ABSTRACT

Provided are a method for efficiently producing an asymmetric conjugated diyne from an inexpensive and safe alternative compound to hydroxylamine hydrochloride and a method for producing a Z,Z-conjugated diene compound from the asymmetric conjugated diyne compound thus obtained. More specifically, provided is a method for producing an asymmetric conjugated diyne compound comprising a step of subjecting a terminal alkyne compound (1): $HC{\equiv}C-Z^1-Y^1$ to a coupling reaction with an alkynyl halide (2): $Y^2-Z^2-C{\equiv}C-X$ by using sodium borohydride in water and an organic solvent in the presence of a copper catalyst and a base to obtain the asymmetric conjugated diyne compound (3): $Y^2-Z^2-C{\equiv}C-C{\equiv}C-Z^1-Y^1$. In addition, provided is a method for producing a Z,Z-conjugated diene compound by reducing the resulting asymmetric conjugated diyne compound, or the like.

9 Claims, No Drawings

METHOD FOR PRODUCING ASYMMETRIC CONJUGATED DIYNE COMPOUND AND METHOD FOR PRODUCING Z,Z-CONJUGATED DIENE COMPOUND USING THE SAME

RELATED APPLICATIONS

This application claims priority from Japanese Application No. 2015-022119, filed Feb. 6, 2015, the contents of each of which is incorporated herein by reference in its entirety.

BACKGROUND OF THE INVENTION

1. Field of the Invention

The present invention relates to a method for producing an asymmetric conjugated diyne compound and a method for producing a Z,Z-conjugated diene compound comprising the same method.

2. Description of the Related Art

An asymmetric conjugated diyne compound is very useful as a film because it can form a corresponding copolymer on the surface of a metal, or as a precursor of natural product such as pheromone because it is present abundantly in such a natural product.

As a method for synthesizing an asymmetric conjugated diyne compound, there are known a method of subjecting an alkynyl halide to a coupling reaction with a terminal alkyne by using a palladium catalyst and a ligand in the presence of a Cu(I) salt (A. Lei et al., J. Am. Chem. Soc. 2008, 130(44), 14713-14720), a method of subjecting two alkynyl halides to a coupling reaction in a N,N-dimethylformamide (DMF) solvent in the presence of potassium iodide and in the absence of a catalyst (H. Jiang et al., J. Org. Chem. 2010, 75(19), 6700-6703), and a method of subjecting an alkynyl halide to a coupling reaction (Cadiot-Chodkiewicz reaction) with a terminal alkyne in the presence of a Cu(I) salt and hydroxylamine (J. P. Marino et al., J. Org. Chem. 2002, 67(19), 6841-6842, WO2008/154642).

SUMMARY OF THE INVENTION

The method disclosed in A. Lei et al., J. Am. Chem. Soc. 2008, 130(44), 14713-14720 is not suited for industrial production because it contains use of an expensive palladium catalyst and a special ligand. The method disclosed in H. Jiang et al., J. Org. Chem. 2010, 75(19), 6700-6703 contains use of only inexpensive reagents without a metal catalyst, but a target asymmetric diyne compound is produced in a yield as low as from 34 to 62% and an undesirable symmetric diyne compound is remarkably produced as a byproduct. The method disclosed in J. P. Marino et al., J. Org. Chem. 2002, 67(19), 6841-6842 contains a reaction in the presence of additional hydroxylamine hydrochloride because the catalyst is deactivated during the reaction. The method disclosed in WO2008/154642 contains a reaction by using the hydroxylamine hydrochloride in an amount equivalent to that of the terminal alkyne. However, the hydroxylamine hydrochloride is not preferred from the standpoint of ensuring safety because even a trace amount of hydroxylamine released therefrom is explosive and many explosion incidents occurred in the past.

With the foregoing in view, the invention has been made. An object of the invention is to provide a method for efficiently producing an asymmetric conjugated diyne compound by using an inexpensive and safe alternative compound to the hydroxylamine hydrochloride. Another object is to provide a method for producing a Z,Z-conjugated diene compound by making use of the same method.

It has been found that an asymmetric conjugated diyne compound can be produced safely in a high yield by subjecting a terminal alkyne compound to a coupling reaction with an alkynyl halide by using sodium borohydride in water and an organic solvent in the presence of a copper catalyst and a base, leading to completion of the invention.

In one aspect of the invention, there is provided a method for producing an asymmetric conjugated diyne compound, comprising a step of subjecting a terminal alkyne compound represented by the following formula (1):

$$HC{\equiv}C{-}Z^1{-}Y^1 \quad (1)$$

wherein $Y^1$ represents a hydrogen atom; a halogen atom; a hydroxyl group; a hydroxyl group protected with a protecting group that forms an ester, ether or acetal; or a formyl group protected with a protecting group that forms thioacetal or acetal; and $Z^1$ represents a linear, branched, cyclic or polycyclic divalent $C_{1-14}$ hydrocarbon group having an optional double bond or triple bond; to a coupling reaction with an alkynyl halide represented by the following formula (2):

$$Y^2{-}Z^2{-}C{\equiv}C{-}X \quad (2)$$

wherein $Y^2$ represents a hydrogen atom; a halogen atom; a hydroxyl group; a hydroxyl group protected with a protecting group that forms an ester, ether or acetal; or a formyl group protected with a protecting group that forms thioacetal or acetal; $Z^2$ represents linear, branched, cyclic or polycyclic divalent $C_{1-14}$ hydrocarbon group having an optional double bond or triple bond; X represents a halogen atom; and the $Y^2{-}Z^2$ is not the same as the $Y^1{-}Z^1$;

by using sodium borohydride in water and an organic solvent in the presence of a copper catalyst and a base to obtain the asymmetric conjugated diyne compound represented by the following formula (3):

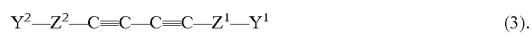

$$Y^2{-}Z^2{-}C{\equiv}C{-}C{\equiv}C{-}Z^1{-}Y^1 \quad (3).$$

In another aspect of the invention, there is also provided a method for producing various Z,Z-conjugated diene compounds by using the asymmetric conjugated diyne compound thus obtained.

According to the present invention, an asymmetric conjugated diyne compound can be produced safely in a high yield by using sodium borohydride which can be used safely at a low cost even if it is added in a large amount, while not using hydroxylamine which is explosive and has markedly lowered explosion temperature when mixed with a trace amount of iron.

DETAILED DESCRIPTION OF THE EMBODIMENTS OF THE INVENTION

The present invention now will be described more fully hereinafter in which embodiments of the invention are provided with reference to the accompanying drawings. This invention may, however, be embodied in many different forms and should not be construed as limited to the embodiments set forth herein; rather, these embodiments are provided so that this disclosure will be thorough and complete, and will fully convey the scope of the invention to those skilled in the art.

The terminology used in the description of the invention herein is for the purpose of describing particular embodiments only and is not intended to be limiting of the invention. As used in the description of the invention and the appended claims, the singular forms "a", "an" and "the" are intended to include the plural forms as well, unless the context clearly indicates otherwise. Unless otherwise defined, all technical and scientific terms used herein have the same meaning as commonly understood by one of ordinary skill in the art to which this invention belongs. All references cited are incorporated herein by reference in their entirety.

In the coupling reaction of the invention, a terminal alkyne compound represented by formula (1) and an alkynyl halide represented by formula (2) are coupled by using sodium borohydride in water and an organic solvent in the presence of a copper catalyst and a base to obtain an asymmetric conjugated diyne compound represented by formula (3).

(1)

(2)

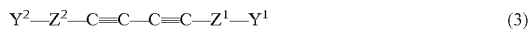
(3)

$Y^1$ and $Y^2$ each represents a hydrogen atom; a halogen atom; a hydroxyl group; a hydroxyl group protected with a protecting group that forms an ester, ether or acetal; or a formyl group protected with a protecting group that forms thioacetal or acetal.

The halogen atom is a fluorine atom, a chlorine atom, a bromine atom or an iodine atom, preferably a chlorine atom, a bromine atom or an iodine atom.

Specific examples of the hydroxyl group protected with a protecting group that forms an ester include an acetoxy group; substituted acetoxy groups such as a trifluoroacetoxy group and a triphenylmethoxyacetoxy group; sulfonyl groups such as a tosyloxy group; a pivaloyloxy group; a benzoyloxy group; and a methoxycarbonyloxy group.

Specific examples of the hydroxyl group protected with a protecting group that forms an ether include a methoxy group; substituted methoxy groups such as a methylthiomethoxy group; siloxy groups such as a trimethylsiloxy group, a triethylsiloxy group, a tert-butyldimethylsiloxy group, a triisopropylsiloxy group and a tert-butyldiphenylsiloxy group; substituted benzyl groups such as a benzyloxy group and a trityloxy group; a p-methoxyphenyloxy group; and an allyloxy group.

Specific examples of the hydroxyl group protected with a protecting group that forms acetal include alkoxymethoxy groups such as a methoxymethoxy group, a tert-butoxymethoxy group, a 2-methoxyethoxymethoxy group, a benzyloxymethoxy group, a p-methoxybenzyloxymethoxy group, and a 2-(trimethylsilyl)ethoxymethoxy group; alkoxyethoxy groups such as an ethoxyethoxy group; and a tetrahydropyranyloxy group.

Specific examples of the formyl group protected with a protecting group that forms thioacetal include monovalent groups obtained by thioacetalizing an aldehyde represented by RCHO into, for example, S,S'-dialkyl dithioacetals such as S,S'-dimethyl dithioacetal and S,S'-diethyl dithioacetal; S,S'-diacetyl dithioacetal; 1,3-dithiane; or 1,3-dithiolane; and by removing R therefrom, Specific examples of the formyl group protected with a protecting group that forms acetal include monovalent groups obtained by acetalizing an aldehyde represented by RCHO into, for example, $C_{2-8}$ dialkyl acetals such as dimethyl acetal, diethyl acetal, dipropyl acetal, dibutyl acetal and diisopropyl acetal; 1,3-dioxolane; substituted 1,3-dioxolanes such as 4-(3-butenyl)-1,3-dioxolane, 4-phenyl-1,3-dioxolane, 4-trimethylsilyl-1,3-dioxolane and (4R,5R)-diphenyl-1,3-dioxolane; 1,3-dioxane; substituted 1,3-dioxanes such as 5,5-dimethyl-1,3-dioxane; O,O'-phenylenedioxy ketal diacetyl acetal; or bis(2-nitrobenzyl); and by removing R therefrom.

$Z^1$ and $Z^2$ each represents a substituted or unsubstituted, linear, branched, cyclic or polycyclic divalent $C_{1-14}$, preferably $C_{2-10}$ hydrocarbon group which may have a double bond or triple bond.

The arbitrary number of hydrogen atoms of these divalent hydrocarbon groups may be substituted by an alkyl group such as a methyl group, an ethyl group, a butyl group, an isobutyl group, a sec-butyl group or a tert-butyl group; an aryl group such as a phenyl group, a tolyl group or a xylyl group; or an aralkyl group such as a benzyl group.

Specific examples of $Z^1$ and $Z^2$ include a 1,2-ethylene group (—$(CH_2)_2$—), a trimethylene group (1,3-propylene group, —$(CH_2)_3$—), a tetramethylene group (1,4-butylene group, —$(CH_2)_4$—), a pentamethylene group (1,5-pentylene group, —$(CH_2)_5$—), a hexamethylene group (1,6-hexylene group, —$(CH_2)_6$—), a heptamethylene group (1,7-heptylene group, —$(CH_2)_7$—), an octamethylene group (1,8-octylene group, —$(CH_2)_8$—), a nonamethylene group [1,9-nonylene group, —$(CH_2)_9$—], a decamethylene group (1,10-decylene group, —$(CH_2)_{10}$—), an undecamethylene group (1,11-undecylene group, —$(CH_2)_{11}$—), a dodecamethylene group (1,12-dodecylene group, —$(CH_2)_{12}$—), a tridecamethylene group (1,13-tridecylene group, —$(CH_2)_{13}$—), a tetradecamethylene group (1,14-tetradecylene group, —$(CH_2)_{14}$—), a butynylene group, a pentenylene group, a hexenylene group, a heptenylene group, an octenylene group, a nonenylene group, and double-bond positional or geometrical isomers of these divalent unsaturated hydrocarbon groups; a hexadienylene group, a heptadienylene group, a nonadienylene group, and double bond positional or geometrical isomers of these divalent unsaturated hydrocarbon groups; a nonatrienylene group, an undecatrienylene group, a dodecatetraenylene group, and double bond positional or geometrical isomers of these divalent unsaturated hydrocarbon groups; methylethylene group (propylene group, —$CH_2$—$CH(CH_3)$—), a 2-methyltrimethylene group (2-methyl-1,3-propylene group), a 2,2-dimethyltrimethylene group (2,2-dimethyl-1,3-propylene group), a cyclohexane-1,2-diyl group, a cyclohexane-1,3-diyl group, a cyclohexane-1,4-diyl group, a 1,2-phenylene group (o-phenylene group), a 1,3-phenylene group (m-phenylene group), a 1,4-phenylene group (p-phenylene group), a 1,2-naphthylene group, a 1,4-naphthylene group, a 2,6-naphthylene group, a 1,4-dimethylbenzene-7,8-diyl group, a cyclopentylene group, a cyclohexylene group, a cycloheptylene group, a cyclooctylene group, a benzylene group, a 1-phenytylene group, a 2-phenytylene group, a 3-phenylpropylene group, a 2-phenylpropylene group, a 1-phenylpropylene group, a phenylene group, a naphthylene group, an anthrylene group, a phenanthrylene group, and a biphenylene group.

Specific examples of the terminal alkyne compounds (1) include 1-propyne, 1-butyne, 1-pentyne, 1-hexyne, 1-heptyne, 1-octyne, 1-nonyne, 1-decyne, 1-undecyne, 1-dodecyne, 3-decen-1-yne, 4-decen-1-yne, 5-decen-1-yne, 6-decen-1-yne, 7-decen-1-yne, 8-decen-1-yne, 9-decen-1-yne, 3,5-tetradecadien-1-yne, 4,6-tetradecadien-1-yne, 4,7-tetradecadien-1-yne, 5,7-tetradecadien-1-yne, 5,8-tetradecadien-1-yne, 5,9-tetradecadien-1-yne, 5,10-tetradecadien-1-yne, 5,11-tetradecadien-1-yne, 5,12-tetradecadien-1-yne, 5,13-tetradecadien-1-yne, 4-chloro-1-butyne, 5-chloro-1-pentyne, 6-chloro-1-hexyne, 7-chloro-1-heptyne, 8-chloro-1-octyne, 9-chloro-1-nonyne, 10-chloro-1-decyne, 11-chloro-1-undecyne, 12-chloro-1-dodecyne, 3-butyn-1-ol, 4-pentyn-1-ol, 5-hexyn-1-ol, 6-heptyn-1-ol, 7-octyn-1-ol, 8-nonyn-1-ol, 9-decyne-1-ol, 10-undecyn-1-ol, 11-dodecyn-1-ol, 3-butynyl acetate, 4-pentynyl acetate, 5-hexynyl acetate, 6-heptynyl acetate, 7-octynyl acetate, 8-nonynyl acetate, 9-decynyl acetate, 10-undecynyl acetate, 11-dodecynyl acetate, 1,1-diethoxy-6-heptyne, 1,1-diethoxy-7-octyne, 1,1-diethoxy-8-nonyne, 1,1-diethoxy-9-decyne, 1,1-diethoxy-10-undecyne, 1,1-diethoxy-11-dodecyne, 1,1-dimethoxy-6-heptyne, 1,1-dimethoxy-7-octyne, 1,1-dimethoxy-8-nonyne, 1,1-dimethoxy-9-decyne, 1,1-dimethoxy-10-undecyne, and 1,1-dimethoxy-11-dodecyne.

X represents a halogen atom such as chlorine atom, bromine atom or iodine atom.

Specific examples of the alkynyl halide (2) include 1-chloro-1-propyne, 1-chloro-1-butyne, 1-chloro-1-pentyne, 1-chloro-1-hexyne, 1-chloro-1-heptyne, 1-chloro-1-octyne, 1-chloro-1-nonyne, 1-chloro-1-decyne, 1-bromo-1-propyne, 1-bromo-1-butyne, 1-bromo-1-pentyne, 1-bromo-1-hexyne, 1-bromo-1-heptyne, 1-bromo-1-octyne, 1-bromo-1-nonyne, 1-bromo-1-decyne, 1-iodo-1-propyne, 1-iodo-1-butyne, 1-iodo-1-pentyne, 1-iodo-1-hexyne, 1-iodo-1-heptyne, 1-iodo-1-octyne, 1-iodo-1-nonyne, 1-iodo-1-decyne, 1-bromo-5-chloro-1-pentyne, 1-bromo-6-chloro-1-hexyne, 1-bromo-7-chloro-1-heptyne, 1-bromo-8-chloro-1-octyne, 4-bromo-3-butyn-1-ol, 5-bromo-4-pentyn-1-ol, 6-bromo-5-hexyn-1-ol, 7-bromo-6-heptyn-1-ol, 8-bromo-7-octyn-1-ol, 9-bromo-8-nonyn-1-ol, 10-bromo-9-decyn-1-ol, 11-bromo-10-undecyn-1-ol, 12-bromo-11-dodecyn-1-ol, 4-bromo-3-butynyl acetate, 5-bromo-4-pentynyl acetate, 6-bromo-5-hexynyl acetate, 7-bromo-6-heptynyl acetate, 8-bromo-7-octynyl acetate, 9-bromo-8-nonyl acetate, 10-bromo-9-decynyl acetate, 11-bromo-10-undecynyl acetate, and 12-bromo-11-dodecynyl acetate.

The alkynyl halide (2) can be used in an amount of preferably from 1.1 to 2.0 mol per mol of the terminal alkyne compound (1). When the amount is less than 1.1 mol, the reaction may not proceed smoothly. When the amount is more than 2 mol, the reagent may be wasted.

Water can be used in an amount of preferably from 400 to 1000 g per mol of the terminal alkyne compound (1). When the amount is less than 400 g, the reaction may not proceed smoothly. When the amount is more than 1000 g, the charged amount may decrease.

Examples of the organic solvent include alcohols such as methanol, ethanol, 1-propanol, 2-propanol, 1-butanol, ethylene glycol monomethyl ether and diethylene glycol monomethyl ether; hydrocarbons such as toluene, hexane, heptane, benzene, xylene and cumene; ethers such as diethyl ether, dibutyl ether, diethylene glycol diethyl ether, diethylene glycol dimethyl ether, tetrahydrofuran, 1,4-dioxane and ethylene glycol dimethyl ether; and polar solvents such as N,N-dimethylformamide, N,N-dimethylacetamide, acetonitrile, dichloromethane, chloroform and trichloroethylene. The alcohols are preferred from the standpoint of reactivity, and methanol and ethanol are particularly preferred. One or more of these organic solvents may be used. The organic solvent may be used singly or in combination of two or more.

The organic solvent may be used in an amount of preferably from 300 to 900 g per mol of the terminal alkyne compound (1). When the amount is less than 300 g, the reaction may not proceed smoothly. When the amount is more than 900 g, the solvent may be wasted and the charged amount may decrease.

Examples of the copper catalyst include copper halides such as cuprous chloride, cuprous bromide, cuprous iodide, cupric chloride, cupric bromide and cupric iodide; and copper salts such as copper cyanide, cuprous acetate and cupric acetate. The copper halides are preferred from the standpoint of reactivity. One or more of these copper catalysts may be used. The copper catalyst may be used singly or in combination of two or more.

The copper catalyst is used in an amount of preferably from 0.05 to 0.2 mol per mol of the terminal alkyne compound (1). When the amount is less than 0.05 mol, the reaction may not proceed smoothly. When the amount is more than 0.2 mol, the reagent may be wasted.

Examples of the base include tertiary amines such as trimethylamine, triethylamine, tributylamine and N,N-diisopropylethylamine; secondary amines such as dimethylamine, diethylamine and dibutylamine; and primary amines such as ethylamine, propylamine, butylamine, hexylamine and heptylamine. The primary amines are preferred from the standpoint of reactivity. One or more of these bases may be used. The base may be used singly or in combination of two or more.

The base can be used in an amount of from 2 to 5 mol per mol of the terminal alkyne compound (1). When the amount is less than 2 mol, the reaction may not proceed smoothly. When the amount is more than 5 mol, the reagent may be wasted.

The sodium borohydride is used in an amount of preferably from 0.05 to 1 mol, more preferably from 0.05 mol to 0.2 mol per mol of the terminal alkyne compound (1). When the amount is less than 0.05 mol, the reaction may not proceed smoothly. When the amount is more than 1 mol, the reagent may be wasted.

The reaction temperature between the terminal alkyne compound (1) and the alkynyl halide (2) is preferably from −30° C. to 40° C., more preferably from −10° C. to 25° C. A preferable reaction time varies depending on the temperature to be selected or reaction scale. The reaction time is usually from 12 to 24 hours.

The reaction between the terminal alkyne compound (1) and the alkynyl halide (2) produces an asymmetric conjugated diyne compound (3) represented by formula (3):

$$Y^2-Z^2-C\equiv C-C\equiv C-Z^1-Y^1 \quad (3)$$

Examples of the asymmetric conjugated diyne compound (3) produced by the reaction between the terminal alkyne compound (1) and the alkynyl halide (2) include 1,1-dialkoxy-11,13-hexadecadiynes, 1,1-dialkoxy-9,11-tetradecadiynes, 2-(9,11-tetradecadiynyloxy)tetrahydropyran, 1-halo-7,9-tetradecadiynes, 12-halo-1-(methoxymethoxy)-3,5-dodecadiynes, 5,7-hexadecadiyne and 7,9-tetradecadiyn-1-ol.

The respective two alkoxy groups of the 1,1-dialkoxy-11,13-hexadecadiyne and the 1,1-dialkoxy-9,11-tetradecadiyne are each independently and preferably a $C_1$-6 alkoxy group such as methoxy, ethoxy, propanoxy, butoxy, pentyloxy and hexyloxy.

Specific examples of the 1,1-dialkoxy-11,13-hexadecadiynes include 1,1-dimethoxy-11,13-hexadecadiyne, 1,1-diethoxy-11,13-hexadecadiyne, 1,1-dipropanoxy-11,13-hexadecadiyne, 1,1-dibutoxy-11,13-hexadecadiyne, 1,1-dipentyloxy-11,13-hexadecadiyne and 1,1-dihexyloxy-11,13-hexadecadiyne.

Specific examples of the 1,1-dialkoxy-9,11-tetradecadiynes include 1,1-dimethoxy-9,11-tetradecadiyne, 1,1-diethoxy-9,11-tetradecadiyne, 1,1-dipropanoxy-9,11-tetradecadiyne, 1,1-dibutoxy-9,11-tetradecadiyne, 1,1-dipentyloxy-9,11-tetradecadiyne, and 1,1-dihexyloxy-9,11-tetradecadiyne.

Specific examples of the 1-halo-7,9-tetradecadiynes include 1-chloro-7,9-tetradecadiyne, 1-bromo-7,9-tetradecadiyne and 1-iodo-7,9-tetradecadiyne.

Specific examples of the 12-halo-1-(methoxymethoxy)-3,5-dodecadiynes include 12-chloro-1-(methoxymethoxy)-3,5-dodecadiyne, 12-bromo-1-(methoxymethoxy)-3,5-dodecadiyne, and 12-iodo-1-(methoxymethoxy)-3,5-dodecadiyne.

When the asymmetric conjugated diyne compound (3) is the 1,1-dialkoxy-11,13-hexadecadiyne, examples of a preferable combination of the terminal alkyne compound (1) and the alkynyl halide (2) include combinations between a 1,1-dialkoxy-11-dodecyne and 1-bromo-1-butyne, between a 1,1-dialkoxy-11-dodecyne and 1-chloro-1-butyne, between a 1,1-dialkoxy-11-dodecyne and 1-iodo-1-butyne, and between 1-butyne and a 1,1-dialkoxy-12-bromo-11-dodecyne.

When the asymmetric conjugated diyne compound (3) is the 1,1-dialkoxy-9,11-tetradecadiyne, examples of a preferable combination of the terminal alkyne compound (1) and the alkynyl halide (2) include combinations between a 1,1-dialkoxy-9-decyne and 1-bromo-1-butyne, between a 1,1-dialkoxy-9-decyne and 1-chloro-1-butyne, between a 1,1-dialkoxy-9-decyne and 1-iodo-1-butyne, and between 1-butyne and 1,1-dialkoxy-10-bromo-9-decyne.

When the asymmetric conjugated diyne compound (3) is the 2-(9,11-tetradecadiynyloxy)tetrahydropyran, examples of a preferable combination of the terminal alkyne compound (1) and the alkynyl halide (2) include combinations between 2-(9-decynyloxy)tetrahydropyran and 1-bromo-1-butyne, between 2-(9-decynyloxy)tetrahydropyran and 1-chloro-1-butyne, between 2-(9-decynyloxy)tetrahydropyran and 1-iodo-1-butyne, and between 1-butyne and 1-bromo-2-(9-decynyloxy)tetrahydropyran.

When the asymmetric conjugated diyne compound (3) is the 1-halo-7,9-tetradecadiyne, examples of a preferable combination of the terminal alkyne compound (1) and the alkynyl halide (2) include combinations between 1-hexyne and a 1-bromo-8-halo-1-octyne, between 1-hexyne and a 1-chloro-8-halo-1-octyne, between 1-hexyne and a 1-iodo-8-halo-1-octyne, between a 1-halo-7-octyne and 1-bromo-1-hexyne, between a 1-halo-7-octyne and 1-chloro-1-hexyne, and between a 1-halo-7-octyne and 1-iodo-1-hexyne.

When the asymmetric conjugated diyne compound (3) is the 12-halo-1-(methoxymethoxy)-3,5-dodecadiyne, examples of a preferable combination of the terminal alkyne compound (1) and the alkynyl halide (2) include combinations between 1-(methoxymethoxy)-3-butyne and 1-bromo-8-chloro-1-octyne, between 1-(methoxymethoxy)-3-butyne and 1-chloro-8-chloro-1-octyne, between 1-(methoxymethoxy)-3-butyne and 1-iodo-8-chloro-1-octyne, and between 1-chloro-7-octyne and 1-bromo-3-(methoxymethoxy)-1-butyne.

When the asymmetric conjugated diyne compound (3) is the 5,7-hexadecadiyne, examples of a preferable combination of the terminal alkyne compound (1) and the alkynyl halide (2) include combinations between 1-decyne and 1-bromo-1-hexyne, between 1-decyne and 1-chloro-1-hexyne, between 1-decyne and 1-iodo-1-hexyne, between 1-hexyne and 1-bromo-1-decyne, between 1-hexyne and 1-chloro-1-decyne, and 1-hexyne and 1-iodo-1-decyne.

When the asymmetric conjugated diyne compound (3) is the 7,9-tetradecadiyn-1-ol, examples of a preferable combination of the terminal alkyne compound (1) and the alkynyl halide (2) include combinations between 7-octyn-1-ol and 1-bromo-1-hexyne, between 7-octyn-1-ol and 1-chloro-1-hexyne, between 7-octyn-1-ol and 1-iodo-1-hexyne, and between 1-hexyne and 1-brom-1-octyn-1-ol.

Using the asymmetric conjugated diyne compounds obtained by using the above-described method, various Z,Z-conjugated diene compounds can be produced. The following are production examples of the Z,Z-conjugated diene compounds.

(11Z,13Z)-11,13-Hexadecadienal can be produced by a method preferably comprising a step of obtaining the above-described 1,1-dialkoxy-11,13-hexadecadiyne, a step of reducing the 1,1-dialkoxy-11,13-hexadecadiyne to obtain a 1,1-dialkoxy-(11Z,13Z)-11,13-hexadecadiene, and a step of hydrolyzing the 1,1-dialkoxy-(11Z,13Z)-11,13-hexadecadiene to obtain the (11Z,13Z)-11,13-hexadecadienal.

The reduction of the 1,1-dialkoxy-11,13-hexadecadiyne can be achieved by hydroboration-protonation with a dialkylborane; hydrosilylation to obtain vinyl silane, followed by desilylation; reduction in an alcohol solvent in the presence of zinc; reduction using potassium hydroxide and N,N-dimethylformamide (DMF) in the presence of a palladium catalyst such as palladium acetate; reduction using diisobutylaluminum hydride (DIBAL) or lithium aluminum hydride (LAH); Birch reduction; or a hydrogenation reaction using a nickel catalyst such as nickel boride, a Lindlar catalyst, a palladium catalyst such as palladium hydroxide or palladium carbon, or a platinum catalyst. Of these, the hydrogenation reaction, the hydroboration-protonation, or the hydrosilylation to obtain vinylsilane, followed by desilylation is preferred from the standpoint of selectivity, and the hydroboration-protonation is more preferred.

In general, in the Birch reduction, the reaction is carried out preferably at a low temperature of from −40 to 0° C. for 1 to 10 hours. In the reduction using diisobutylaluminum hydride or zinc, the reaction is carried out preferably at a temperature of from 0 to 100° C. for 1 to 12 hour. In the reduction using a palladium catalyst and potassium hydroxide, the reaction is carried out preferably at a temperature of from 100 to 180° C. for 6 to 20 hours.

A preferable hydrogenation reaction temperature varies depending on the catalyst to be used, and is usually from 20 to 80° C. A preferable reaction time varies depending on the reaction temperature or reaction scale, and is usually from 5 to 20 hours.

The hydrosilylation is carried out using a trialkylsilane and a metal catalyst such as Wilkinson catalyst or Trost catalyst. A preferable hydrosilylation reaction temperature is from 5° C. to 100° C. A preferably reaction time varies depending on the reaction scale and is usually from 2 to 12 hours. The desilylation after hydrosilylation is carried out preferably at from 5 to 80° C. usually for 1 to 8 hours while using an acid such as hydrogen iodide, acetyl chloride, sulfuric acid or hydrochloric acid; titanium tetrachloride; or iodine.

The dialkylborane to be used for hydroboration has preferably from 4 to 12 carbon atoms, more preferably from 8 to 12 carbon atoms. Specific examples of the dialkylborane include dicyclohexylborane, disiamylborane, and 9-borabicyclo[3.3.1]nonane (9-BBN).

A preferable reaction temperature of the hydroboration is from −20° C. to 20° C. A preferable reaction time varies depending on the reaction temperature or reaction scale, and is usually from 3 to 12 hours.

Protonation after the hydroboration can be carried out using a carboxylic acid such as acetic acid, trifluoroacetic acid, chloroacetic acid, formic acid, oxalic acid and p-toluenesulfonic acid; or a mineral acid such as sulfuric acid, hydrochloric acid, nitric acid and phosphoric acid. Of these, the carboxylic acid is preferred from the standpoint of reactivity.

A preferable reaction temperature of the protonation varies depending on a reagent to be used and is from 0° C. to 150° C. A preferable reaction time varies depending on the reaction temperature and reaction scale, and is usually from 1 to 12 hours.

The hydrolysis of the 1,1-dialkoxy-(11Z,13Z)-11,13-hexadecadiene is carried out using water and an acid such as hydrochloric acid, oxalic acid, p-toluenesulfonic acid, acetic acid, formic acid, trifluoroacetic acid and sulfuric acid. A preferable reaction temperature of the hydrolysis is from 0° C. to 180° C. The optimum reaction temperature varies depending on the acid to be used. A preferable reaction time varies depending on the acid to be used or the reaction scale, and is usually from 1 to 8 hours.

(9Z,11Z)-9,11-Tetradecadienal can be produced by a method preferably comprising a step of obtaining the above-described 1,1-dialkoxy-9,11-tetradecadiyne, a step of reducing the 1,1-dialkoxy-9,11-tetradecadiyne to obtain a 1,1-dialkoxy-(9Z,11Z)-9,11-tetradecadiene, and a step of hydrolyzing the 1,1-dialkoxy-(9Z,11Z)-9,11-tetradecadiene to obtain the (9Z,11Z)-9,11-tetradecadienal.

Reaction conditions of the reduction reaction and the hydrolysis reaction are similar to those employed in the step of obtaining the (11Z,13Z)-11,13-hexadecadienal.

(9Z,11Z)-9,11-Tetradecadienyl acetate is produced by a method preferably comprising a step of obtaining the above-described 2-(9,11-tetradecadiynyloxy)tetrahydropyran, a step of reducing the 2-(9,11-tetradecadiynyloxy)tetrahydropyran to obtain 2-((9Z,11Z)-9,11-tetradecadienyloxy)tetrahydropyran, a step of deprotecting the 2-((9Z,11Z)-9,11-tetradecadienyloxy)tetrahydropyran for removal of the tetrahydropyranyl group therefrom to obtain (9Z,11Z)-9,11-tetradecadienol, and a step of acetylating the (9Z,11Z)-9,11-tetradecadienol to obtain the (9Z,11Z)-9,11-tetradecadienyl acetate.

The reduction of the 2-(9,11-tetradecadiynyloxy)tetrahydropyran is similar to that in the step of obtaining the (11Z,13Z)-11,13-hexadecadienal.

The deprotection of the 2-((9Z,11Z)-9,11-tetradecadienyloxy)tetrahydropyran for removal of the tetrahydropyranyl group therefrom is carried out using an acid such as acetic acid, p-toluenesulfonic acid and Amberlyst, and an alcohol such as methanol and ethanol. A preferable reaction temperature of the deprotection is from 0° C. to 70° C.

The acetylation of the (9Z,11Z)-9,11-tetradecadienol is achieved by the reaction with an acetylating agent. Examples of the acetylating agent include acetic anhydride and acetyl chloride. The acetylation reaction can be carried out, for example, by reacting the (9Z,11Z)-9,11-tetradecadienol with acetic anhydride in a solvent in the presence of a pyridine compound or amine compound. A preferable reaction temperature of this reaction is from 10° C. to 100° C. The acetylation may also be carried out by reacting the (9Z,11Z)-9,11-tetradecadienol with sodium hydride or potassium hydride in a solvent, and then reacting with acetyl chloride. In this case, a preferable reaction temperature is from 0° C. to 40° C.

EXAMPLES

The invention will hereinafter be described specifically based on Examples. It should not be construed that it is limited to or by Examples.

Example 1: Production of $(CH_3CH_2O)_2CH(CH_2)_9$
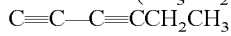
$C\equiv C-C\equiv CCH_2CH_3$ Butylamine (6.58 g, 0.09 mol), cuprous chloride (0.30 g, 0.003 mol) and water (21 g) were added to a reactor and stirred at 0 to 10° C. for 20 minutes. After stirring, sodium borohydride (0.15 g, 0.0039 mol) was added thereto and the resulting mixture was stirred at 0 to 10° C. for 20 minutes. Then 1,1-diethoxy-11-dodecyne (7.63 g, 0.03 mol) and methanol (18 g) were added thereto and the resulting mixture was stirred at from 0 to 10° C. for 15 minutes. After stirring, 1-bromo-1-butyne (4.39 g, 0.033 mol) was added dropwise thereto at 0 to 10° C. After completion of the dropwise addition, the reaction mixture was stirred at 0 to 10° C. for 10 hours. Hexane (9.78 g) was then added to the reaction mixture for separation into an organic phase. The organic phase was concentrated under reduced pressure and the resulting residue was purified by column chromatography to obtain 1,1-diethoxy-11,13-hexadecadiyne (8.54 g, 0.028 mol) in a yield of 92.9%.

[Nuclear magnetic resonance spectrum] $^1$H-NMR (500 MHz, CDCl$_3$): δ=1.14 (3H, t, J=7.3 Hz), 1.19 (6H, t, J=7.3 Hz), 1.22-1.40 (12H, m), 1.49 (2H, tt, J=7.3, 7.3 Hz), 1.56-1.61 (2H, m), 2.22 (2H, t, J=7.3 Hz), 2.24 (2H, q, J=7.3 Hz), 3.47 (2H, dq, J=7.0, 7.3 Hz), 3.62 (2H, dq, J=7.0, 7.3 Hz), 4.46 (1H, t, J=6.1 Hz); $^{13}$C-NMR (125 MHz, CDCl$_3$): δ=12.86, 13.38, 15.32, 19.14, 24.70, 28.29, 28.77, 29.02, 29.34, 29.41, 29.46, 33.55, 60.77, 64.65, 65.12, 77.62, 78.55, 102.93

[Mass spectrum] EI-mass spectrum (70 eV): m/z 306 (M$^+$), 216, 103, 75, 43, 29

[Infrared absorption spectrum] (NaCl): ν=2928, 2856, 1456, 1128, 1105, 1061

Example 2: Production of $(CH_3CH_2O)_2CH(CH_2)_7$
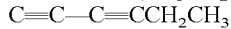
$C\equiv C-C\equiv CCH_2CH_3$ Butylamine (6.58 g, 0.09 mol), cuprous chloride (0.30 g, 0.003 mol) and water (21 g) were added to a reactor and stirred at 0 to 10° C. for 20 minutes. After stirring, sodium borohydride (0.15 g, 0.0039 mol) was added thereto and the resulting mixture was stirred at 0 to 10° C. for 20 minutes. Then 1,1-diethoxy-9-decyne (6.79 g, 0.03 mol) and methanol (18 g) were added thereto and stirred at 0 to 10° C. for 15 minutes. After stirring, 1-bromo-1-butyne (4.39 g, 0.033 mol) was added dropwise thereto at 0 to 10° C. After completion of the dropwise addition, the reaction mixture was stirred at from 0 to 10° C. for 11 hours. Hexane (9.78 g) was then added to the reaction mixture for separation into an organic phase. The organic phase was concentrated under reduced pressure and the resulting residue was purified by column chromatography to obtain 1,1-diethoxy-9,11-tetradecadiyne (6.86 g, 0.025 mol) in a yield of 82.0%.

[Nuclear magnetic resonance spectrum] $^1$H-NMR (500 MHz, CDCl$_3$): δ=1.14 (3H, t, J=7.6 Hz), 1.19 (6H, t, J=7.3 Hz), 1.23-1.40 (8H, m), 1.49 (2H, tt, J=7.3, 7.3 Hz), 1.55-1.61 (2H, m), 2.22 (2H, t, J=7.3 Hz), 2.24 (2H, q, J=7.6 Hz), 3.47 (2H, dq, J=4.6, 7.3 Hz), 3.62 (2H, dq, J=4.6, 7.3 Hz), 4.46 (1H, t, J=5.8 Hz); $^{13}$C-NMR (125 MHz, CDCl$_3$): δ=12.86, 13.37, 15.32, 19.12, 24.64, 28.25, 28.69, 28.97, 29.26, 33.52, 60.78, 64.64, 65.16, 77.56, 78.55, 102.89

[Mass spectrum] EI-mass spectrum (70 eV): m/z 278 (M$^+$), 233, 103, 75, 47, 29

[Infrared absorption spectrum] (NaCl): ν=2975, 2932, 1457, 1373, 1128, 1062

Example 3: Production of Cl—CH$_2$(CH$_2$)$_5$C≡C—C≡C(CH$_2$)$_3$CH$_3$

Butylamine (4.39 g, 0.06 mol), cuprous chloride (0.20 g, 0.002 mol) and water (14 g) were added to a reactor and stirred at 0 to 10° C. for 20 minutes. After stirring, sodium borohydride (0.098 g, 0.0026 mol) was added thereto and the resulting mixture was stirred at 0 to 10° C. for 20 minutes. After stirring, 1-hexyne (1.64 g, 0.02 mol) and methanol (12 g) were added thereto and the resulting mixture was stirred at 0 to 10° C. for 15 minutes. After stirring, 1-bromo-8-chloro-1-octyne (4.92 g, 0.022 mol) was added dropwise at 0 to 10° C. After completion of the dropwise addition, the reaction mixture was stirred at 0 to 10° C. for 15 hours. Hexane (12 g) and water (14 g) were then added to the reaction mixture for separation into an organic phase. The organic phase was concentrated under reduced pressure and the resulting residue was purified by column chromatography to obtain 1-chloro-7,9-tetradecadiyne (4.44 g, 0.0198 mol) in a yield of 98.8%.

[Nuclear magnetic resonance spectrum] $^1$H-NMR (500 MHz, CDCl$_3$): δ=0.90 (3H, t, J=7.3 Hz), 1.34-1.46 (6H, m), 1.50 (2H, tt, J=7.3, 7.3 Hz), 1.51 (2H, tt, J=7.3, 7.3 Hz), 1.77 (2H, tt, J=6.9, 6.9 Hz), 2.24 (2H, t, J=6.9 Hz), 2.25 (2H, t, J=6.9 Hz), 3.52 (2H, t, J=6.9 Hz); $^{13}$C-NMR (125 MHz, CDCl$_3$): δ=13.48, 18.84, 19.07, 21.88, 26.33, 28.01, 28.09, 30.33, 32.41, 44.95, 65.14, 65.46, 77.04, 77.60

[Mass spectrum] EI-mass spectrum (70 eV): m/z 224 (M$^+$), 161, 119, 105, 91, 41

[Infrared absorption spectrum] (NaCl): ν=2935, 2861, 1463, 728, 652

Example 4: Production of CH$_3$OCH$_2$O—(CH$_2$)$_2$C≡C—C≡C(CH$_2$)$_5$CH$_2$Cl

Butylamine (4.39 g, 0.06 mol), cuprous chloride (0.20 g, 0.002 mol) and water (14 g) were added to a reactor and stirred at −10 to 5° C. for 20 minutes. After stirring, sodium borohydride (0.098 g, 0.0026 mol) was added thereto and the resulting mixture was then stirred at −10 to 5° C. for 20 minutes. Then 1-(methoxymethoxy)-3-butyne (2.28 g, 0.02 mol) and methanol (12 g) were then added thereto and the resulting mixture was stirred at −10 to 0° C. for 15 minutes. After stirring, 1-bromo-8-chloro-1-octyne (4.92 g, 0.022 mol) was added thereto dropwise at −10 to 10° C. After completion of the dropwise addition, the reaction mixture was stirred at −10 to 0° C. for 15 hours. Hexane (12 g) and water (14 g) were then added to the reaction mixture for separation into an organic phase. The organic phase was concentrated under reduced pressure and the resulting residue was purified by column chromatography to obtain 12-chloro-1-(methoxymethoxy)-3,5-dodecadiyne (5.06 g, 0.0197 mol) in a yield of 98.5%.

[Nuclear magnetic resonance spectrum] $^1$H-NMR (500 MHz, CDCl$_3$): δ=1.37-1.46 (4H, m), 1.52 (2H, tt, J=6.9, 6.9 Hz), 1.76 (2H, tt, J=6.9, 6.9 Hz), 2.24 (2H, t, J=6.9 Hz), 2.54 (2H, t, J=6.9 Hz), 3.36 (3H, s), 3.52 (2H, t, J=6.9 Hz), 3.63 (2H, t, J=6.9 Hz), 4.63 (2H, s); $^{13}$C-NMR (125 MHz, CDCl$_3$): δ=19.03, 20.77, 26.29, 27.97, 27.99, 32.38, 44.92, 55.27, 65.26, 65.51, 66.27, 73.95, 77.61, 96.38

[Mass spectrum] EI-mass spectrum (70 eV): m/z 255 (M$^+$−1), 194, 105, 91, 45

[Infrared absorption spectrum] (NaCl): ν=2937, 2862, 1463, 1150, 1111, 1070, 1031, 728, 650

Example 5: Production of THPO-CH$_2$(CH$_2$)$_7$C≡C—C≡CCH$_2$CH$_3$

Butylamine (169.6 g, 2.32 mol), cuprous chloride (7.65 g, 0.077 mol) and water (541 g) were added to a reactor and stirred at 0 to 10° C. for 20 minutes. After stirring, sodium borohydride (3.80 g, 0.10 mol) was added thereto and the resulting mixture was stirred at 0 to 10° C. for 20 minutes. Then 2-(9-decynyloxy)tetrahydropyran (184.2 g, 0.77 mol) and methanol (464 g) were then added thereto and the resulting mixture was stirred at 0 to 10° C. for 15 minutes. After stirring, a solution of 1-bromo-1-butyne (113.1 g, 0.85 mol) in THF and toluene was added dropwise thereto at from 0 to 10° C. After completion of the dropwise addition, the reaction mixture was stirred at 0 to 10° C. for 12 hours. Hexane (464 g) and water (541 g) were then added to the reaction mixture for separation into an organic phase. The organic phase was concentrated under reduced pressure and the resulting residue was purified by column chromatography to obtain 2-(9,11-tetradecadiynyloxy)tetrahydropyran (200.2 g, 0.69 mol) in a yield of 89.2%.

[Nuclear magnetic resonance spectrum] $^1$H-NMR (500 MHz, CDCl$_3$): δ=1.14 (3H, t, J=6.9 Hz), 1.21-1.42 (8H, m), 1.45-1.63 (8H, m), 1.70 (1H, dt, J=13, 3.4 Hz), 1.77-1.86 (1H, m), 2.23 (2H, q, J=6.9 Hz), 2.25 (2H, t, J=7.3 Hz), 3.36 (1H, dt, J=9.6, 6.7 Hz), 3.45-3.52 (1H, m), 3.71 (1H, dt, J=9.8, 6.9 Hz), 3.82-3.89 (1H, m), 4.56 (1H, t, J=3.4 Hz); $^{13}$C-NMR (125 MHz, CDCl$_3$): δ=12.86, 13.38, 19.13, 19.67, 25.47, 26.14, 28.27, 28.72, 28.98, 29.25, 29.68, 30.75, 62.28, 64.65, 65.16, 67.58, 77.58, 78.55, 98.80

[Mass spectrum] EI-mass spectrum (70 eV): m/z 290 (M$^+$), 261, 105, 85, 41

[Infrared absorption spectrum] (NaCl): ν=2935, 2856, 1455, 1136, 1120, 1078, 1033

Example 6: Production of Cl—CH$_2$(CH$_2$)$_5$C≡C—C≡C(CH$_2$)$_3$CH$_3$

Butylamine (4.39 g, 0.06 mol), cuprous chloride (0.20 g, 0.002 mol) and water (14 g) were added to a reactor and stirred at 0 to 10° C. for 20 minutes. After stirring, sodium borohydride (0.098 g, 0.0026 mol) was added thereto and the resulting mixture was stirred at 0 to 10° C. for 20 minutes. Then 1-chloro-7-octyne (2.89 g, 0.02 mol) and methanol (12 g) were added thereto and the resulting mixture was stirred at 0 to 10° C. for 15 minutes. After stirring, 1-bromo-1-hexyne (3.54 g, 0.022 mol) was added dropwise thereto at 0 to 10° C. After completion of the dropwise addition, the reaction mixture was stirred at 0 to 10° C. for 15 hours. Hexane (12 g) and water (14 g) were then added to the reaction mixture for separation into an organic phase. The organic phase was concentrated under reduced pressure and the resulting residue was purified by column chromatography to obtain 1-chloro-7,9-tetradecadiyne (4.21 g, 0.0187 mol) in a yield of 93.6%.

[Nuclear magnetic resonance spectrum] $^1$H-NMR (500 MHz, CDCl$_3$): δ=0.90 (3H, t, J=7.3 Hz), 1.34-1.46 (6H, m), 1.50 (2H, tt, J=7.3, 7.3 Hz), 1.51 (2H, tt, J=7.3, 7.3 Hz), 1.77 (2H, tt, J=6.9, 6.9 Hz), 2.24 (2H, t, J=6.9 Hz), 2.25 (2H, t, J=6.9 Hz), 3.52 (2H, t, J=6.9 Hz); $^{13}$C-NMR (125 MHz, CDCl$_3$): δ=13.48, 18.84, 19.07, 21.88, 26.33, 28.01, 28.09, 30.33, 32.41, 44.95, 65.14, 65.46, 77.04, 77.60

[Mass spectrum] EI-mass spectrum (70 eV): m/z 224 (M$^+$), 161, 119, 105, 91, 41

[Infrared absorption spectrum] (NaCl): ν=2935, 2861, 1463, 728, 652

Example 7: Production of CH$_3$(CH$_2$)$_3$C≡C—C≡C(CH$_2$)$_7$CH$_3$

Butylamine (4.39 g, 0.06 mol), cuprous chloride (0.20 g, 0.002 mol) and water (14 g) were added to a reactor and stirred at 0 to 10° C. for 20 minutes. After stirring, sodium borohydride (0.098 g, 0.0026 mol) was added thereto and stirred at 0 to 10° C. for 20 minutes. Then 1-decyne (2.67 g, 0.02 mol) and methanol (12 g) were then added thereto and the resulting mixture was stirred at 0 to 10° C. for 15 minutes. After stirring, 1-bromo-1-hexyne (3.54 g, 0.022 mol) was added dropwise at 0 to 10° C. After completion of the dropwise addition, the reaction mixture was stirred at 0 to 10° C. for 6 hours and then further stirred at room temperature for 40 hours. Hexane (12 g) and water (14 g) were then added to the reaction mixture for separation into an organic phase. The organic phase was concentrated under reduced pressure and the resulting residue was purified by column chromatography to obtain 5,7-hexadecadiyne (3.12 g, 0.0143 mol) in a yield of 71.4%.

[Nuclear magnetic resonance spectrum] $^1$H-NMR (500 MHz, CDCl$_3$): δ=0.88 (3H, t, J=7.3 Hz), 0.90 (3H, t, J=7.3 Hz), 1.18-1.32 (8H, m), 1.33-1.41 (2H, m), 1.42 (2H, tt, J=7.3, 7.3 Hz), 1.46-1.55 (4H, m), 2.23 (2H, t, J=6.9 Hz), 2.25 (2H, t, J=6.9 Hz); $^{13}$C-NMR (125 MHz, CDCl$_3$): δ=13.49, 14.06, 18.86, 19.18, 21.90, 22.63, 28.35, 28.84, 29.05, 29.13, 30.38, 31.81, 65.22, 65.24, 77.43, 77.50

[Mass spectrum] EI-mass spectrum (70 eV): m/z 219 (M$^+$), 189, 175, 161, 147, 133, 119, 105, 91, 41

[Infrared absorption spectrum] (NaCl): ν=2928, 2857, 1465

Example 8: Production of HO—CH$_2$(CH$_2$)$_5$C≡C—C≡C(CH$_2$)$_3$CH$_3$

Butylamine (4.39 g, 0.06 mol), cuprous chloride (0.20 g, 0.002 mol) and water (14 g) were added to a reactor and stirred at 0 to 10° C. for 20 minutes. After stirring, sodium borohydride (0.098 g, 0.0026 mol) was added thereto and stirred at 0 to 10° C. for 20 minutes. Then 7-octyn-1-ol (2.52 g, 0.02 mol) and methanol (12 g) were then added thereto and the resulting mixture was stirred at 0 to 10° C. for 15 minutes. After stirring, 1-bromo-1-hexyne (3.54 g, 0.022 mol) was added dropwise thereto at 0 to 10° C. After completion of the dropwise addition, the reaction mixture was stirred at 0 to 10° C. for 3 hours. Hexane (12 g) and water (14 g) were then added to the reaction mixture for separation into an organic phase. The organic phase was concentrated under reduced pressure and the resulting residue was purified by column chromatography to obtain 7,9-tetradecadiyn-1-ol (3.01 g, 0.0146 mol) in a yield of 73.0%.

[Nuclear magnetic resonance spectrum] $^1$H-NMR (500 MHz, CDCl$_3$): δ=0.89 (3H, t, J=7.3 Hz), 1.31-1.44 (2H, m), 1.36 (2H, tt, J=7.3, 7.3 Hz), 1.40 (2H, tt, J=7.3, 7.3 Hz), 1.46-1.59 (2H, m), 1.49 (2H, tt, J=7.3, 7.3 Hz), 1.52 (1H, br), 1.55 (2H, tt, J=7.3, 7.3 Hz), 2.24 (4H, t, J=7.3 Hz), 3.62 (2H, t, J=6.9 Hz); $^{13}$C-NMR (125 MHz, CDCl$_3$): δ=13.47, 18.82, 19.07, 21.86, 25.19, 28.21, 28.53, 30.32, 32.52, 62.81, 65.15, 65.33, 77.22, 77.52

[Mass spectrum] EI-mass spectrum (70 eV): m/z 205 (M$^+$–1), 163, 149, 105, 91, 41

[Infrared absorption spectrum] (NaCl): ν=3332, 2933, 2860, 1463, 1055

Example 9: Production of OHC—CH$_2$(CH$_2$)$_8$CH═CH—CH═CHCH$_2$CH$_3$

N,N-diethylaniline borane (64.0 g, 0.39 mol) and THF (127 g) were added to a reactor and stirred at 10° C. or less for 30 minutes. After stirring, cyclohexene (65.8 g, 0.80 mol) was added thereto and the resulting mixture was stirred at 10° C. or less for 2 hours. Then 1,1-diethoxy-11,13-hexadecadiyne (40.1 g, 0.13 mol) was added dropwise thereto and the resulting mixture was stirred at 10° C. or less for 6 hours and then further stirred at room temperature for 14 hours. After addition of acetic acid (43.6 g, 0.73 mol) thereto, followed by stirring at 50° C. to 70° C. for 2 hours, the reaction mixture was cooled to 20° C. or less and subjected to addition of a 25% aqueous sodium hydroxide solution (498 g). Then a 30% hydrogen peroxide solution (68.6 g, 0.61 mol) was added thereto and the resulting mixture was stirred for 2 hours. Water (311 g) and hexane (102 g) were then added to the reaction mixture for separation into an organic phase. The organic phase was washed successively with water (311 g) and a saturated aqueous sodium chloride solution (311 g), and then concentrated under reduced pressure to obtain a residue. The residue thus obtained, THF (321 g), water (321 g) and oxalic acid (32.2 g, 0.36 mol) were added to the reactor, stirred at 60° C. for one hour, and separated into an organic phase. The organic phase was concentrated under reduced pressure and the resulting residue was purified by distillation to obtain (11Z,13Z)-11,13-hexadecadienal (19.2 g, 0.081 mol) in a yield of 62.0%.

[Nuclear magnetic resonance spectrum] $^1$H-NMR (500 MHz, CDCl$_3$): δ=0.99 (3H, t, J=7.3 Hz), 1.22-1.34 (10H, m), 1.37 (2H, tt, J=7.3, 7.3 Hz), 1.62 (2H, tt, J=7.3, 7.3 Hz), 2.17 (2H, dt, J=7.3, 7.3 Hz), 2.18 (2H, dt, J=7.7, 7.7 Hz), 2.41 (2H, dt, J=1.9, 7.3 Hz), 5.43 (1H, dt, J=9.6, 7.7 Hz), 5.43 (1H, dt, J=9.6, 7.7 Hz), 6.22 (1H, ddd, J=8.0, 8.0, 1.5 Hz), 6.22 (1H, ddd, J=9.6, 9.6, 1.5 Hz), 9.75 (1H, t, J=1.9 Hz); $^{13}$C-NMR (125 MHz, CDCl$_3$): δ=14.16, 20.74, 22.04, 27.41, 29.11, 29.19, 29.28, 29.32, 29.37, 29.58, 43.87, 122.97, 123.43, 132.04, 133.57, 202.84

[Mass spectrum] EI-mass spectrum (70 eV): m/z 236 (M$^+$), 207, 95, 67, 55, 29

[Infrared absorption spectrum] (NaCl): ν=2926, 2854, 1727, 1463, 721

Example 10: Production of OHC—CH$_2$(CH$_2$)$_6$CH═CH—CH═CHCH$_2$CH$_3$

N,N-diethylaniline borane (33.2 g, 0.20 mol) and THF (56.5 g) were added to a reactor and the resulting mixture was stirred at 10° C. or less for 30 minutes. After stirring, cyclohexene (34.0 g, 0.41 mol) was added thereto and the resulting mixture was stirred at 10° C. or less for 2 hours. Then 1,1-diethoxy-9,11-tetradecadiyne (16.2 g, 0.058 mol) was added dropwise thereto, and the resulting mixture was stirred at 10° C. or less for 8 hours and then stirred at room temperature for 12 hours. After addition of acetic acid (24.1 g, 0.40 mol) thereto, followed by stirring at 50° C. to 70° C. for 2 hours and cooling to 20° C. or less, a 25% aqueous sodium hydroxide solution (80 g) was added to the reaction mixture. A 30% aqueous hydrogen peroxide solution (53.8 g, 0.47 mol) was then added thereto and the resulting mixture was stirred for 1 hour. Then water (106 g) and hexane (100 g) were added to the reaction mixture for separation into an organic phase. The organic phase was washed successively with water (200 g) and a saturated aqueous sodium chloride solution (200 g), and then concentrated under reduced pressure to obtain a residue. The residue thus obtained, THF (409 g) and oxalic acid (40.9 g, 0.45 mol) were added to the reactor, stirred at 60° C. for 3 hours, and separated into an organic phase. The organic phase was concentrated under reduced pressure and the resulting residue was purified by chromatography to obtain (9Z,11Z)-9,11-tetradecadienal (8.22 g, 0.039 mol) in a yield of 67.9%.

[Nuclear magnetic resonance spectrum] $^1$H-NMR (500 MHz, CDCl$_3$): δ=0.99 (3H, t, J=7.7 Hz), 1.27-1.33 (6H, m), 1.37 (2H, tt, J=6.5, 6.5 Hz), 1.62 (2H, tt, J=7.3, 7.3 Hz), 2.170 (2H, dt, J=7.7, 7.7 Hz), 2.172 (2H, dt, J=7.3, 7.3 Hz), 2.40 (2H, dt, J=1.9, 7.3 Hz), 5.38-5.48 (2H, m), 6.21 (1H, ddd, J=11.1, 11.1, 1.5 Hz), 6.21 (1H, ddd, J=10.1, 10.1, 1.5 Hz), 9.75 (1H, t, J=1.9 Hz); $^{13}$C-NMR (125 MHz, CDCl$_3$): δ=14.15, 20.74, 22.01, 27.34, 28.97, 29.05, 29.15, 29.48, 43.84, 122.93, 123.53, 131.87, 133.65, 202.77

[Mass spectrum] EI-mass spectrum (70 eV): m/z 208 (M$^+$), 109, 95, 82, 67, 55, 29

[Infrared absorption spectrum] (NaCl): ν=2929, 2855, 1727, 1463, 720

Example 11A: Production of HO—CH$_2$(CH$_2$)$_7$ CH=CH—CH=CHCH$_2$CH$_3$

N,N-diethylaniline borane (234.8 g, 1.44 mol) and THF (467 g) were added to a reactor and the resulting mixture was stirred at 10° C. or less for 30 minutes. After stirring, cyclohexene (241.3 g, 2.94 mol) was added thereto and the resulting mixture was stirred at 10° C. or less for 2 hours. Then 2-(9,11-tetradecadiynyloxy)tetrahydropyran (139.4 g, 0.48 mol) was added dropwise, and the resulting mixture was stirred at 10° C. or less for 8 hours and then further stirred at room temperature for 12 hours. After addition of acetic acid (170.1 g, 2.83 mol) thereto, followed by stirring at 50° C. to 70° C. for 2 hours and cooling to 20° C. or less, a 25% aqueous sodium hydroxide solution (499.2 g) was added to the reaction mixture. A 30% aqueous hydrogen peroxide solution (380.9 g, 3.36 mol) was then added thereto and the resulting mixture was stirred for 2 hours. Then water (749 g) and hexane (240 g) were added to the reaction mixture for separation into an organic phase. The organic phase was washed successively with water (1217 g) and a saturated aqueous sodium chloride solution (1217 g), and then concentrated under reduced pressure to obtain a residue. The residue thus obtained, methanol (700 g) and p-toluene sulfonic acid monohydrate (2 g) were added to the reactor and stirred at room temperature for 18 hours. A 25% aqueous sodium hydroxide solution (50 g), water (500 g) and hexane (500 g) were then added to the reaction mixture for separation into an organic phase. The organic phase was concentrated under reduced pressure and the resulting residue was purified by distillation to obtain (9Z,11Z)-9,11-tetradecadienol (42.3 g, 0.20 mol) in a yield of 41.9%.

[Nuclear magnetic resonance spectrum] $^1$H-NMR (500 MHz, CDCl$_3$): δ=0.99 (3H, t, J=7.3 Hz), 1.24-1.41 (10H, m), 1.45 (1H, br), 1.55 (2H, tt, J=6.9, 6.9 Hz), 2.17 (2H, dt, J=7.7, 7.7 Hz), 2.16 (2H, dq, J=7.3, 7.3 Hz), 3.62 (2H, t, J=6.9 Hz), 5.43 (1H, dt, J=9.9, 7.7 Hz), 5.43 (1H, dt, J=9.9, 7.7 Hz), 6.220 (1H, ddd, J=9.9, 9.9, 1.5 Hz), 6.223 (1H, ddd, J=8.1, 8.1, 1.5 Hz); $^{13}$C-NMR (125 MHz, CDCl$_3$): δ=14.16, 20.74, 25.68, 27.41, 29.17, 29.34, 29.41, 29.58, 32.74, 62.99, 122.97, 123.43, 132.05, 133.59

[Mass spectrum] EI-mass spectrum (70 eV): m/z 210 (M$^+$), 192, 95, 82, 67, 55, 29

[Infrared absorption spectrum] (NaCl): ν=3338, 2927, 2854, 1463, 1057, 721

Example 11B: Production of AcO—CH$_2$(CH$_2$)$_7$ CH=CH—CH=CHCH$_2$CH$_3$

Pyridine (24.3 g, 0.31 mol), toluene (19 g) and (9Z,11Z)-9,11-tetradecadienol (35.9 g, 0.17 mol) were added to a reactor and stirred at room temperature for 20 minutes. Acetic anhydride (22.7 g, 0.22 mol) was then added thereto, followed by stirring at from 20 to 40° C. for 5 hours. Water (46 g) was then added to the reaction mixture for separation into an organic phase. The organic phase was concentrated under reduced pressure and the resulting residue was purified by distillation to obtain (9Z,11Z)-9,11-tetradecadienyl acetate (36.3 g, 0.14 mol) in a yield of 84.2%.

[Nuclear magnetic resonance spectrum] $^1$H-NMR (500 MHz, CDCl$_3$): δ=0.99 (3H, t, J=7.3 Hz), 1.25-1.44 (10H, m), 1.61 (2H, tt, J=7.3, 7.3 Hz), 2.04 (3H, s), 2.16 (2H, dq, J=7.3, 7.3 Hz), 2.17 (2H, dt, J=7.3, 7.3 Hz), 4.04 (2H, t, J=6.9 Hz), 5.43 (1H, dt, J=9.4, 7.3 Hz), 5.43 (1H, dt, J=9.8, 7.3 Hz), 6.220 (1H, ddd, 9.4, 9.4, 1.5 Hz), 6.223 (1H, ddd, 9.4, 9.4, 1.5 Hz); $^{13}$C-NMR (125 MHz, CDCl$_3$): δ=14.16, 20.74, 20.97, 25.85, 27.39, 28.55, 29.13, 29.15, 29.32, 29.55, 64.59, 122.96, 123.46, 131.99, 133.60, 171.17

[Mass spectrum] EI-mass spectrum (70 eV): m/z 252 (M$^+$), 192, 96, 82, 67, 29

[Infrared absorption spectrum] (NaCl): ν=2929, 2855, 1742, 1463, 1238, 1037, 721

Having thus described certain embodiments of the present invention, it is to be understood that the invention defined by the appended claims is not to be limited by particular details set forth in the above description as many apparent variations thereof are possible without departing from the spirit or scope thereof as hereinafter claimed.

The invention claimed is:

1. A method for producing an asymmetric conjugated diyne compound, comprising:
   a step of subjecting a terminal alkyne compound of formula (1):

wherein Y$^1$ is a hydrogen atom; a halogen atom; a hydroxyl group; a hydroxyl group protected with a protecting group that forms an ester, ether or acetal; or a formyl group protected with a protecting group that forms thioacetal or acetal; and Z$^1$ is a linear, branched, cyclic or polycyclic divalent C$_{1-14}$ hydrocarbon group having an optional double bond or triple bond;
   to a coupling reaction with an alkynyl halide of formula (2):

wherein Y$^2$ is a hydrogen atom; a halogen atom; a hydroxyl group; a hydroxyl group protected with a protecting group that forms an ester, ether or acetal; or a formyl group protected with a protecting group that forms thioacetal or acetal; Z$^2$ is a linear, branched, cyclic or polycyclic divalent C$_{1-14}$ hydrocarbon group having an optional double bond or triple bond; X is a halogen atom; and the Y$^2$—Z$^2$ is not the same as the Y$^1$—Z$^1$;
   by using sodium borohydride in water and an organic solvent in the presence of a copper salt and a base to obtain the asymmetric conjugated diyne compound of formula (3):

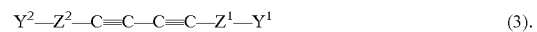

2. The method for producing an asymmetric conjugated diyne compound according to claim 1, wherein an amount of the sodium borohydride is from 0.05 to 1 mol per mol of the terminal alkyne compound (1).

3. The method for producing an asymmetric conjugated diyne compound according to claim 1, wherein the organic solvent is one or more alcohols.

4. The method for producing an asymmetric conjugated diyne compound according to claim 1, wherein the asymmetric conjugated diyne is a 1,1-dialkoxy-11,13-hexadecadiyne, 1,1-dialkoxy-9,11-tetradecadiyne, or 2-(9,11-tetradecadiynyloxy)tetrahydropyran.

5. A method for producing (11Z,13Z)-11,13-hexadecadienal, comprising:
   a step of obtaining a 1,1-dialkoxy-11,13-hexadecadiyne by the method according to claim 4;
   a step of reducing the 1,1-dialkoxy-11,13-hexadecadiyne to obtain a 1,1-dialkoxy-(11Z,13Z)-11,13-hexadecadiene; and
   a step of hydrolyzing the 1,1-dialkoxy-(11Z,13Z)-11,13-hexadecadiene to obtain the (11Z,13Z)-11,13-hexadecadienal.

6. A method for producing (9Z,11Z)-9,11-tetradecadienal, comprising:
   a step of obtaining a 1,1-dialkoxy-9,11-tetradecadiyne by the method according to claim 4;
   a step of reducing the 1,1-dialkoxy-9,11-tetradecadiyne to obtain a 1,1-dialkoxy-(9Z,11Z)-9,11-tetradecadiene; and
   a step of hydrolyzing the 1,1-dialkoxy-(9Z,11Z)-9,11-tetradecadiene to obtain the (9Z,11Z)-9,11-tetradecadienal.

7. A method for producing (9Z,11Z)-9,11-tetradecadienyl acetate, comprising:
   a step of obtaining 2-(9,11-tetradecadiynyloxy)tetrahydropyran by the method according to claim 4;
   a step of reducing the 2-(9,11-tetradecadiynyloxy)tetrahydropyran to obtain 2-((9Z,11Z)-9,11-tetradecadienyloxy)tetrahydropyran;
   a step of deprotecting the 2-((9Z,11Z)-9,11-tetradecadienyloxy)tetrahydropyran for removal of a tetrahydropyranyl group to obtain (9Z,11Z)-9,11-tetradecadienol; and
   a step of acetylating the (9Z,11Z)-9,11-tetradecadienol to obtain the (9Z,11Z)-9,11-tetradecadienyl acetate.

8. The method for producing an asymmetric conjugated diyne compound according to claim 1, wherein the copper salt is a copper halide.

9. The method for producing an asymmetric conjugated diyne compound according to claim 1, wherein the copper salt is cuprous chloride.

\* \* \* \* \*

UNITED STATES PATENT AND TRADEMARK OFFICE
CERTIFICATE OF CORRECTION

PATENT NO. : 9,845,304 B2
APPLICATION NO. : 15/014598
DATED : December 19, 2017
INVENTOR(S) : Miyake et al.

It is certified that error appears in the above-identified patent and that said Letters Patent is hereby corrected as shown below:

In the Specification

Column 3, Line 26: Please correct "Y2-Z2-C☐C-X (2)" to read -- Y2-Z2-C≡C-X (2) --

Column 6, Line 62: Please correct "$C_1$-6" to read -- $C_{1-6}$ --

Signed and Sealed this
Nineteenth Day of June, 2018

Andrei Iancu
*Director of the United States Patent and Trademark Office*